(12) United States Patent
Itkowitz et al.

(10) Patent No.: US 12,016,646 B2
(45) Date of Patent: Jun. 25, 2024

(54) LAYERED FUNCTIONALITY FOR A USER INPUT MECHANISM IN A COMPUTER-ASSISTED SURGICAL SYSTEM

(71) Applicant: Intuitive Surgical Operations, Inc., Sunnyvale, CA (US)

(72) Inventors: Brandon D. Itkowitz, San Jose, CA (US); Adrian N. Bedard, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 379 days.

(21) Appl. No.: 17/438,055

(22) PCT Filed: Mar. 12, 2019

(86) PCT No.: PCT/US2019/021948
§ 371 (c)(1),
(2) Date: Sep. 10, 2021

(87) PCT Pub. No.: WO2020/185218
PCT Pub. Date: Sep. 17, 2020

(65) Prior Publication Data
US 2022/0015851 A1   Jan. 20, 2022

(51) Int. Cl.
*G06F 17/00*   (2019.01)
*A61B 34/00*   (2016.01)
(Continued)

(52) U.S. Cl.
CPC .............. *A61B 34/74* (2016.02); *A61B 34/20* (2016.02); *A61B 90/37* (2016.02); *G06F 3/011* (2013.01); *A61B 2090/373* (2016.02)

(58) Field of Classification Search
CPC ......... A61B 34/74; A61B 34/20; A61B 90/37; A61B 2090/373; A61B 34/25;
(Continued)

(56) References Cited

U.S. PATENT DOCUMENTS 8,004,229 B2 * 8/2011 Nowlin ............... A61B 90/37
                                            318/568.2
9,386,983 B2 * 7/2016 Swensgard ........... A61B 34/30
(Continued)

FOREIGN PATENT DOCUMENTS

KR       101876386 B1     7/2018
WO   WO-2012151585 A2    11/2012
WO   WO-2018216501 A1 * 11/2018 ......... A61B 1/00188

OTHER PUBLICATIONS

Accurate Parameter Estimation for Master-Slave Operation of a Surgical Robot (Year: 2021).*
(Continued)

*Primary Examiner* — Ronnie M Mancho

(57) ABSTRACT

A computer-assisted surgical system includes a function selection system configured to detect an actuation and a de-actuation of a user input mechanism associated with a user control mechanism for controlling a surgical instrument coupled to a manipulator arm of a computer-assisted surgical system, the user input mechanism configured to facilitate activation and deactivation of a clutch mode of operation in which the user control mechanism is decoupled from controlling the surgical instrument. Based on the detecting of the actuation and the de-actuation of the user input mechanism, the function selection system determines information associated with the user input mechanism and the user control mechanism, compares the information to a set of defined criteria, and performs, when the information satisfies the set of defined criteria, a function associated with a different mode of operation of the computer assisted surgical system.

20 Claims, 6 Drawing Sheets

(51) Int. Cl.
*A61B 34/20* (2016.01)
*A61B 90/00* (2016.01)
*G06F 3/01* (2006.01)

(58) Field of Classification Search
CPC ........ A61B 2034/741; A61B 2090/061; A61B 34/70; A61B 34/35; G06F 3/011
USPC .......................................................... 700/245
See application file for complete search history.

(56) References Cited

U.S. PATENT DOCUMENTS

| | | | | |
|---|---|---|---|---|
| 9,517,106 | B2* | 12/2016 | Hourtash | A61B 34/25 |
| 9,579,088 | B2* | 2/2017 | Farritor | A61B 34/74 |
| 11,389,171 | B2* | 7/2022 | Goldsmith | A61B 17/3468 |
| 11,424,027 | B2* | 8/2022 | Shelton, IV | A61B 17/072 |
| 11,510,741 | B2* | 11/2022 | Shelton, IV | A61B 17/0206 |
| 2006/0167440 | A1* | 7/2006 | Cooper | A61B 34/71 |
| | | | | 606/1 |
| 2006/0276686 | A1* | 12/2006 | Tsuji | A61B 5/064 |
| | | | | 600/117 |
| 2009/0088775 | A1 | 4/2009 | Swarup et al. | |
| 2009/0163948 | A1* | 6/2009 | Sunaoshi | A61B 34/70 |
| | | | | 606/205 |
| 2010/0174410 | A1* | 7/2010 | Greer | A61B 34/37 |
| | | | | 700/264 |
| 2010/0234857 | A1* | 9/2010 | Itkowitz | G09B 23/285 |
| | | | | 700/259 |
| 2011/0118752 | A1 | 5/2011 | Itkowitz et al. | |
| 2011/0118753 | A1 | 5/2011 | Itkowitz et al. | |
| 2012/0179169 | A1 | 7/2012 | Swarup et al. | |
| 2013/0024024 | A1* | 1/2013 | Namiki | A61B 1/00149 |
| | | | | 700/245 |
| 2013/0211590 | A1* | 8/2013 | Diolaiti | A61B 34/30 |
| | | | | 700/257 |
| 2013/0303892 | A1* | 11/2013 | Zhao | A61B 5/7425 |
| | | | | 600/424 |
| 2013/0345718 | A1* | 12/2013 | Crawford | A61B 17/8866 |
| | | | | 606/130 |
| 2016/0100898 | A1* | 4/2016 | Jinno | A61B 34/37 |
| | | | | 606/130 |
| 2017/0129108 | A1 | 5/2017 | Diolaiti et al. | |
| 2018/0280076 | A1 | 10/2018 | Trees et al. | |
| 2018/0280099 | A1 | 10/2018 | Cone et al. | |
| 2022/0015851 | A1* | 1/2022 | Itkowitz | G06F 3/011 |

OTHER PUBLICATIONS

Research and Realization of a Master-Slave Robotic System for Retinal Vascular Bypass Surgery (Year: 2018).*
Reconfigurability and Reconfigurable Manufacturing Systems—State-of-the-art Review (Year: 2004).*
International Preliminary Report on Patentability for Application No. PCT/US2019/021948, dated Sep. 23, 2021, 7 pages.
International Search Report and Written Opinion for Application No. PCT/US2019/021948, dated Dec. 10, 2019, 12 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. EP20190919306, dated Oct. 11, 2022, 10 pages.

* cited by examiner

LAYERED FUNCTIONALITY FOR A USER INPUT MECHANISM IN A COMPUTER-ASSISTED SURGICAL SYSTEM

RELATED APPLICATIONS

The present application is a U.S. National Stage Application under 35 U.S.C. § 371 of International Application No. PCT/US2019/021948, filed on Mar. 12, 2019, the contents of which are hereby incorporated by reference in their entirety.

BACKGROUND INFORMATION

A computer-assisted surgical system allows a surgeon to control telemanipulated surgical instruments to perform a surgical procedure on a patient. The surgeon uses master controls of the computer-assisted surgical system to control movement of the surgical instruments to perform the surgical procedure.

The computer-assisted surgical system may have user input mechanisms (e.g., buttons or the like) through which the surgeon can control additional functionality of the computer-assisted surgical system, such as user input mechanisms for selecting functions of the computer-assisted surgical system to be performed. It is desirable that such user input mechanisms are intuitive and convenient for the surgeon to use and do not impede or overly complicate operation of the master controls of the computer-assisted surgical system.

SUMMARY

An exemplary system includes a processor and a memory storing instructions and a processor communicatively coupled to the memory and configured to execute the instructions to detect an actuation and a de-actuation of a user input mechanism associated with a user control mechanism for controlling a surgical instrument coupled to a manipulator arm of a computer-assisted surgical system, the user input mechanism configured to facilitate activation and deactivation of a clutch mode of operation in which the user control mechanism is decoupled from controlling the surgical instrument, determine, based on the detecting of the actuation and the de-actuation of the user input mechanism, information associated with the user input mechanism and the user control mechanism, compare the information to a set of defined criteria, and perform, when the information satisfies the set of defined criteria, a function associated with a different mode of operation of the computer-assisted surgical system.

An exemplary non-transitory computer-readable medium stores instructions that, when executed, direct at least one processor of a computing device to detect a first input received by way of a user input mechanism associated with a user control mechanism for controlling a surgical instrument coupled to a manipulator arm of a computer-assisted surgical system, the user input mechanism configured to facilitate activation and deactivation of a clutch mode of operation in which the user control mechanism is decoupled from controlling the surgical instrument, determine, based on the detecting of the first input, a first set of information associated with the user input mechanism and the user control mechanism, detect a second input received by way of the user input mechanism, determine, based on the detecting of the second input, a second set of information associated with the user input mechanism and the user control mechanism, compare the first set of information and the second set of information to a set of defined criteria, and perform, when the set of defined criteria is satisfied, a function associated with a different mode of operation of the computer-assisted surgical system.

An exemplary method includes detecting an actuation and a de-actuation of a user input mechanism associated with a user control mechanism for controlling a surgical instrument coupled to a manipulator arm of a computer-assisted surgical system, the user input mechanism configured to facilitate activation and deactivation of a clutch mode of operation in which the user control mechanism is decoupled from controlling the surgical instrument, determining, based on the detecting of the actuation and the de-actuation of the user input mechanism, information associated with the user input mechanism and the user control mechanism, comparing the information to a set of defined criteria and performing, when the information satisfies the set of defined criteria, a function associated with a different mode of operation of the computer-assisted surgical system.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
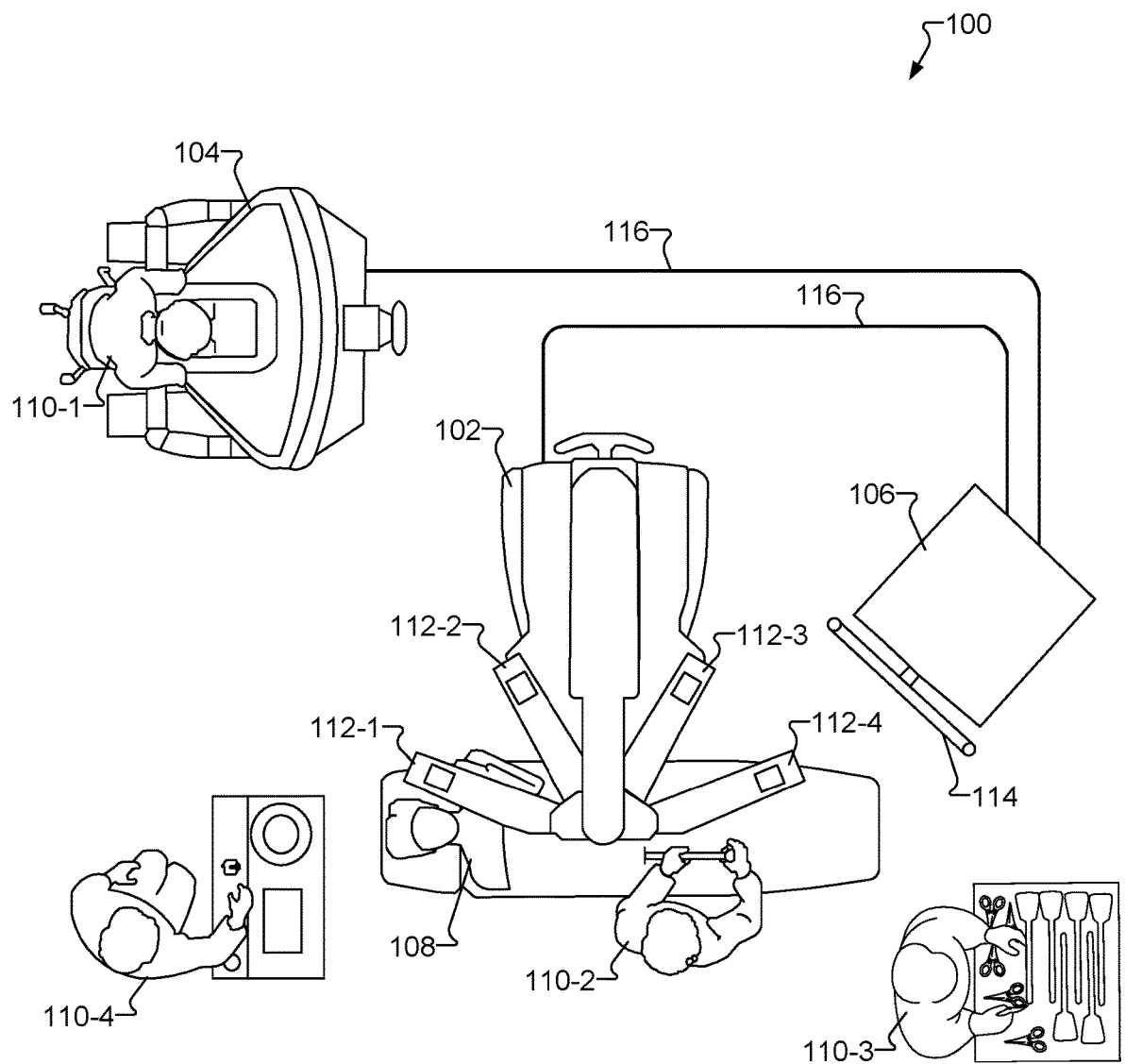
FIG. 1 illustrates an exemplary computer-assisted surgical system according to principles described herein.

Systems and methods for providing layered functionality for a user input mechanism of a computer-assisted surgical system are described herein. Based on the layered functionality of the user input mechanism, a user of the computer-assisted surgical system may intuitively and/or efficiently select functions of the computer-assisted surgical system to be performed. In certain implementations, for example, the computer-assisted surgical system may include a control mechanism, such as a set of one or more master controls, through which a surgeon may provide input to telemanipulate a surgical instrument that is coupled to the control mechanism. The computer-assisted surgical system may further include a user input mechanism associated with (e.g., situated on) the control mechanism and through which a surgeon may provide input to indicate one or more layered functions mapped to the user input mechanism to be performed by the computer-assisted surgical system. In certain examples, the computer-assisted surgical system may be configured to process input received by way of the user input mechanism, as well as information associated with the input (e.g., contextual information such as information about movement of the control mechanism that is associated with the input), to determine which of the various layered functions to perform. The computer-assisted surgical system may be configured to process the input and associated information in a manner that supports use of a single user input mechanism, such as a single, binary-option user input mechanism, for user selection of any of multiple layered functions mapped to the user input mechanism that are to be performed.

As an example, the computer-assisted surgical system may provide a normal mode of operation in which a control mechanism such as a set of master controls may be manipulated by a surgeon to telemanipulate a surgical instrument that is coupled to a manipulator arm of the computer-assisted surgical system. The computer-assisted surgical system may also provide a clutch mode of operation in which the master controls are decoupled from manipulating the surgical instrument such that the surgeon may manipulate (e.g., reposition) the master controls without affecting the surgical instrument (e.g., without moving or otherwise telemanipulating the surgical instrument). The computer-assisted surgical system may include a user input mechanism configured to facilitate activation and deactivation of the clutch mode of operation. In addition to facilitating activation and deactivation of the clutch mode of operation, the user input mechanism may be configured to facilitate user selection of one or more additional functions to be performed by the computer-assisted surgical system.

The user input mechanism may be a single, binary-option user input mechanism associated with a control mechanism such as a set of master controls. To illustrate one example, the user input mechanism may be a button situated on a control mechanism such as a set of master controls. The computer-assisted surgical system may be configured such that the surgeon can choose to operate computer-assisted surgical system in the clutch mode operation by actuating and holding the button (e.g., by pressing the button and holding it down) while the surgeon manipulates the master controls. The same button may also be used by the surgeon to indicate another function of the computer-assisted surgical system to be performed. For example, a momentary actuation and de-actuation of the button that satisfies a set of defined criteria, such as a quick click of the button that satisfies the criteria, may be mapped to another function of the computer-assisted surgical system such that a momentary actuation and de-actuation of the button that satisfies the defined criteria will trigger a performance of the function.

To this end, the computer-assisted surgical system may receive information associated with user interactions with the button (e.g., pressing, releasing, holding), as well as information associated with the master controls (e.g., position, movement, velocity), and determine whether the user interactions with the button satisfy the defined criteria, which may indicate whether the surgeon intended to indicate another function of the computer-assisted surgical system to be performed, such as a function associated with another mode of operation different from the clutch mode of operation. Additionally, such information can be used by the system to determine if an interaction with the button was unintentional.

By accessing and using additional information associated with the user input mechanism and the master controls, the computer-assisted surgical system may reliably and/or accurately select and perform one or more functions of the computer-assisted surgical system that the surgeon intended to be performed. Further, by processing the received input using additional information as described herein, the computer-assisted surgical system may allow a surgeon to activate various modes of operation and or initiate performance of various functions associated with different modes of operation using the same input mechanism, which may allow for fewer and/or more useful user input mechanisms and a simple and uncluttered interface that is intuitive to use. Intuitive interfaces may allow a surgeon to perform fewer unintended actions and/or perform intended actions more easily, which may result in convenient and/or intuitive operation of the computer-assisted surgical system, as well as more efficient surgical procedures. This may allow the computer-assisted surgical system to have a compact and flexible mechanical design (e.g., a design that allows multiple degrees of motion for hands of a surgeon manipulating master controls) and may help keep to a minimum the number of user input mechanisms that are implemented by the computer-assisted surgical system. These and other advantages and benefits of the systems and methods described herein will be made apparent.

FIG. 1 illustrates an exemplary computer-assisted surgical system 100 ("surgical system 100"). As shown, surgical system 100 may include a manipulating system 102, a user control system 104, and an auxiliary system 106 communicatively coupled one to another. Surgical system 100 may be utilized by a surgical team to perform a computer-assisted surgical procedure on a patient 108. As shown, the surgical team may include a surgeon 110-1, an assistant 110-2, a nurse 110-3, and an anesthesiologist 110-4, all of whom may be collectively referred to as "surgical team members 110." Additional or alternative surgical team members may be present during a surgical session as may serve a particular implementation.

While FIG. 1 illustrates an ongoing minimally invasive surgical procedure, it will be understood that surgical system 100 may similarly be used to perform open surgical procedures or other types of surgical procedures that may similarly benefit from the accuracy and convenience of surgical system 100. Additionally, it will be understood that the surgical session throughout which surgical system 100 may be employed may not only include an operative phase of a surgical procedure, as is illustrated in FIG. 1, but may also include preoperative, postoperative, and/or other suitable phases of the surgical procedure. A surgical procedure may include any procedure in which manual and/or instrumental techniques are used on a patient to investigate or treat a physical condition of the patient.

As shown in FIG. 1, manipulating system 102 may include a plurality of manipulator arms 112 (e.g., manipulator arms 112-1 through 112-4) to which a plurality of surgical instruments may be coupled. Each surgical instrument may be implemented by any suitable surgical tool (e.g., a tool having tissue-interaction functions), medical tool, imaging device (e.g., an endoscope), sensing instrument (e.g., a force-sensing surgical instrument), diagnostic instrument, or the like that may be used for a computer-assisted surgical procedure on patient 108 (e.g., by being at least partially inserted into patient 108 and manipulated to perform a computer-assisted surgical procedure on patient 108). While manipulating system 102 is depicted and described herein as including four manipulator arms 112, it will be recognized that manipulating system 102 may include only a single manipulator arm 112 or any other number of manipulator arms as may serve a particular implementation.

Manipulator arms 112 and/or surgical instruments attached to manipulator arms 112 may include one or more displacement transducers, orientational sensors, and/or positional sensors used to generate raw (i.e., uncorrected) kinematics information. One or more components of surgical system 100 may be configured to use the kinematics information to track (e.g., determine positions of) and/or control the surgical instruments.

User control system 104 may be configured to facilitate control by surgeon 110-1 of manipulator arms 112 and surgical instruments attached to manipulator arms 112. For example, surgeon 110-1 may interact with user control system 104 to remotely move or telemanipulate manipulator arms 112 and the surgical instruments. To this end, user control system 104 may provide surgeon 110-1 with imagery (e.g., high-definition 3D imagery) of a surgical area associated with patient 108 as captured by an imaging system (e.g., an endoscope or any other suitable medical imaging system). In certain examples, user control system 104 may include a stereo viewer having two displays where stereoscopic images of a surgical area associated with patient 108 and generated by a stereoscopic imaging system may be viewed by surgeon 110-1. Surgeon 110-1 may utilize the imagery to perform one or more procedures with one or more surgical instruments attached to manipulator arms 112.

To facilitate control of surgical instruments, user control system 104 may include a control mechanism such as a set of master controls. The master controls may be manipulated by surgeon 110-1 to control movement of surgical instruments (e.g., by utilizing robotic and/or teleoperation technology). The master controls may be configured to detect a wide variety of hand, wrist, and finger movements by surgeon 110-1. In this manner, surgeon 110-1 may intuitively perform a procedure using one or more surgical instruments.

Auxiliary system 106 may include one or more computing devices configured to perform primary processing operations of surgical system 100. In such configurations, the one or more computing devices included in auxiliary system 106 may control and/or coordinate operations performed by various other components (e.g., manipulating system 102 and user control system 104) of surgical system 100. For example, a computing device included in user control system 104 may transmit instructions to manipulating system 102 by way of the one or more computing devices included in auxiliary system 106. As another example, auxiliary system 106 may receive, from manipulating system 102, and process image data representative of imagery captured by an imaging device attached to one of manipulator arms 112.

In some examples, auxiliary system 106 may be configured to present visual content to surgical team members 110 who may not have access to the images provided to surgeon 110-1 at user control system 104. To this end, auxiliary system 106 may include a display monitor 114 configured to display one or more user interfaces, such as images (e.g., 2D images) of the surgical area, information associated with patient 108 and/or the surgical procedure, and/or any other visual content as may serve a particular implementation. For example, display monitor 114 may display images of the surgical area together with additional content (e.g., graphical content, contextual information, etc.) concurrently displayed with the images. In some embodiments, display monitor 114 is implemented by a touchscreen display with which surgical team members 110 may interact (e.g., by way of touch gestures) to provide user input to surgical system 100.

Manipulating system 102, user control system 104, and auxiliary system 106 may be communicatively coupled one to another in any suitable manner. For example, as shown in FIG. 1, manipulating system 102, user control system 104, and auxiliary system 106 may be communicatively coupled by way of control lines 116, which may represent any wired or wireless communication link as may serve a particular implementation. To this end, manipulating system 102, user control system 104, and auxiliary system 106 may each include one or more wired or wireless communication interfaces, such as one or more local area network interfaces, Wi-Fi network interfaces, cellular interfaces, etc.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media. Such a non-transitory computer-readable medium storing computer-readable instructions may be implemented by one or more components of surgical system 100.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 2:
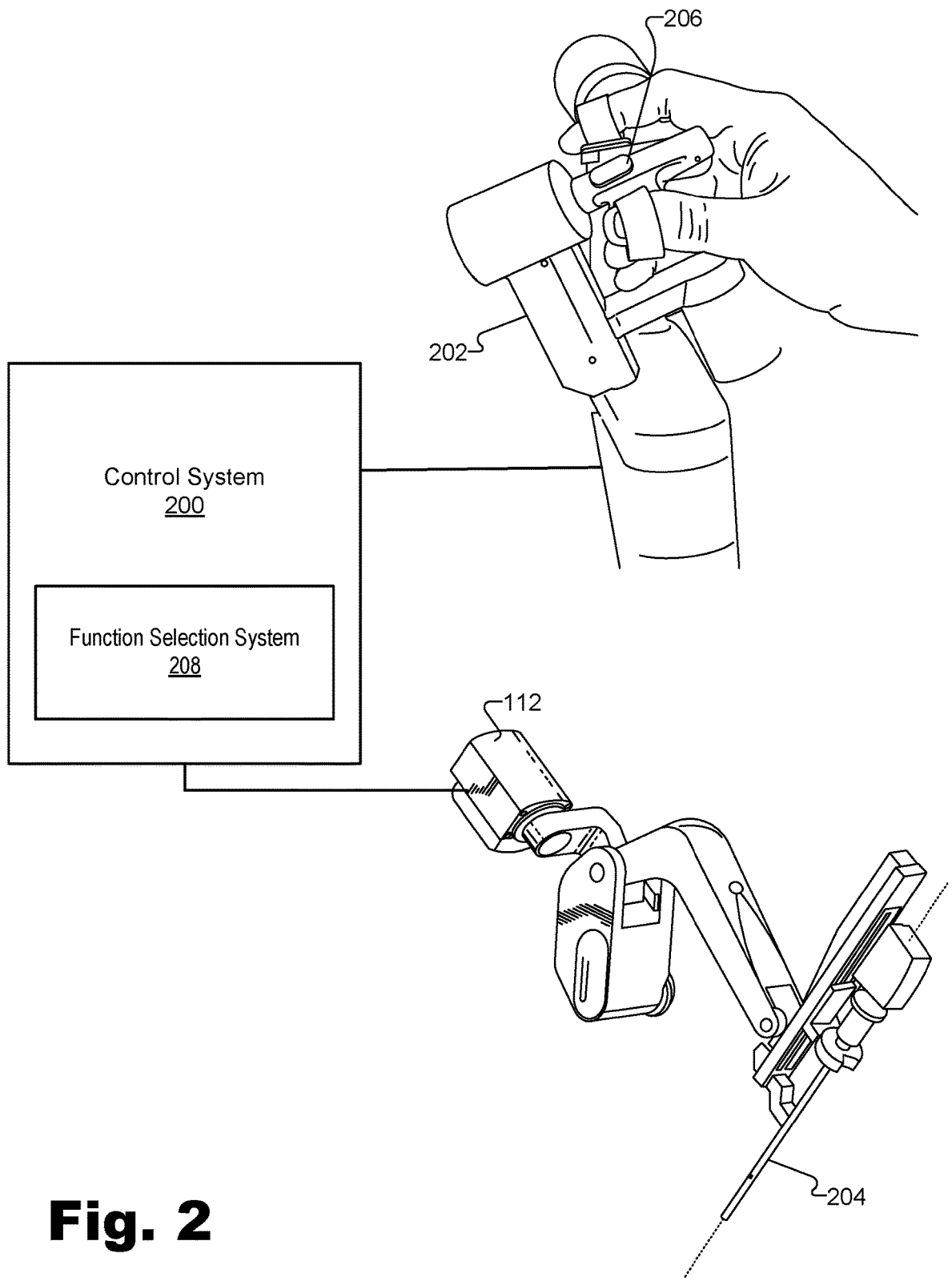
FIG. 2 illustrates an exemplary control system that may be included within the computer-assisted surgical system of FIG. 1 according to principles described herein.

FIG. 2 illustrates an exemplary control system 200 communicatively coupled to a user control mechanism 202 and a manipulator arm 112. Control system 200 may be communicatively coupled to user control mechanism 202 and manipulator arm 112 in any suitable way that allows data, communications, and/or other signals to be sent by control system 200 to user control mechanism 202 and manipulator arm 112 and/or to be received by control system 200 from user control mechanism 202 and manipulator arm 112.

Control system 200 may be implemented within one or more components of surgical system 100, such as within user control system 104, auxiliary system 106, manipulating system 102, or any combination thereof. Control system 200 may be implemented as hardware, software, or a combination of hardware and software configured to perform one or more of the operations described herein, including operations for processing user input received by way of user control mechanism 202 and determining operations of surgical system 100 based on the user input. For example, control system 200 may be configured to translate movements of user control mechanism 202 into movements of manipulator arm 112 and/or a surgical instrument 204 attached to manipulator arm 112.

Manipulator arm 112 may be a manipulator arm of a computer-assisted surgical system, such as any of manipulator arms 112-1 through 112-4 of surgical system 100. Any suitable surgical instrument, such as surgical instrument 204, may be physically coupled to manipulator arm 112 in any suitable way.

User control mechanism 202 may be part of user control system 104 of surgical system 100. For example, user control mechanism 202 may include or be included in a set of master controls of user control system 104. In certain examples, for instance, user control mechanism 202 may be a portion of a set of master controls configured to be manipulated by a surgeon to control movement of surgical instruments. For example, user control mechanism 202 may be configured to be manipulated by a hand of a surgeon to telemanipulate a surgical instrument attached to a manipulator arm, and the set of master controls may include additional controls for controlling movement of surgical instruments, such as another user control mechanism 202 configured to be manipulated by the other hand of the surgeon to telemanipulate another surgical instrument attached to another manipulator arm. Although FIG. 2 illustrates user control mechanism 202 configured to be manipulated by one hand of a surgeon, in other examples a user control mechanism may be a set of master controls that includes multiple mechanisms configured to be manipulated to control movement of surgical instruments. Hence, a user control mechanism, as used herein, may refer to a portion of a set of master controls or to an entire set of master controls.

User control mechanism 202 may include a variety of mechanisms (e.g., buttons, finger loops, levers, pivot points, etc.) configured to receive a wide variety of hand, wrist, and finger movements by a surgeon to control movement of surgical instruments. Accordingly, a surgeon may manipulate user control mechanism 202 in various ways and with multiple degrees of freedom in order to telemanipulate surgical instrument 204 that is coupled to user control mechanism 202 by way of manipulator arm 112 and control system 200.

Additionally, user control mechanism 202 includes a user input mechanism 206 by which the surgeon may provide input to indicate various modes of operation. User input mechanism 206 may be implemented as a button situated on user control mechanism 202, as illustrated. Alternatively or additionally, user input mechanism 206 may be implemented as any type of input mechanism, such as a switch, a toggle input, a directional pad, a joystick, etc. Further, while user input mechanism 206 is shown as a part of user control mechanism 202 (e.g., situated on user control mechanism 202), user input mechanism 206 may alternatively or additionally include input mechanisms separate from user control mechanism 202, such as a foot pedal, a voice input mechanism, or any other suitable input mechanism.

In certain implementations, user input mechanism 206 may include a binary input mechanism having exactly two different mechanical positions (e.g., on and off positions, actuated and non-actuated positions, etc.) that are mapped to discrete input options and that may be selected by user actuation and/or de-actuation of user input mechanism 206. For example, user input mechanism 206 may include a button (e.g., a spring-loaded button), a switch (e.g., a spring-loaded switch), a slider (e.g., a spring-loaded slider), a pedal (e.g., a spring-loaded pedal), or the like. Such an input mechanism may facilitate discrete and momentary input to select from two binary options (e.g., two mechanical positions).

User input mechanism 206 may be associated with user control mechanism 202 in any suitable way. For example, user input mechanism 206 may be disposed on user control mechanism 202 such that user input mechanism 206 is readily accessible by a surgeon using user control mechanism 202 to telemanipulate surgical instrument 204. As an alternative example, user input mechanism 206 may be associated with user control mechanism 202 by virtue of both user input mechanism 206 and user control mechanism 202 being components of the same computer-assisted surgical system. For instance, user input mechanism 206 may be a foot pedal that may be actuated and de-actuated by a user of the computer-assisted surgical system.

Control system 200 is configured to receive information from user control mechanism 202. For example, control system 200 may receive information regarding position, movement, etc. of user control mechanism 202 and/or information regarding user interaction with user control mechanism 202. Based on such information, control system 200 may track the position, movement, and/or other attributes of user control mechanism 202.

Control system 200 may also receive information from manipulator arm 112, such as information regarding movement, pressure, and/or other attributes of manipulator arm 112. In certain examples and/or modes of operation, control system 200 may process the information received from manipulator arm 112 and provide corresponding information and/or signals to user control mechanism 202 to provide feedback (e.g., haptic feedback) to the surgeon.

When operating in certain operating modes (e.g., a normal mode of operation), control system 200 may process the information received from user control mechanism 202 to generate information and/or signals to send to manipulator arm 112 to cause manipulator arm 112 and/or surgical instrument 204 to operate in accordance with the information received from user control mechanism 202. In this or a similar manner, control system 200 may translate attributes of user control mechanism 202 into corresponding operations of manipulator arm 112 and surgical instrument 204, such as by translating movement of user control mechanism 202 into corresponding movement of manipulator arm 112 and surgical instrument 204. In this way, control system 200 couples user control mechanism 202 to manipulator arm 112 such that a surgeon may telemanipulate surgical instrument 204 attached to manipulator arm 112 using user control mechanism 202.

When operating in certain operating modes, control system 200 may output different information to manipulator arm 112 and/or may output information to other components of the surgical system (e.g., one or more display components). When operating in some operating modes, control system 200 may output no information to manipulator arm 112, such as when operating in a clutch mode of operation in which control system 200 decouples user control mechanism 202 from controlling movement of manipulator arm 112 and surgical instrument 204. Examples of operating modes of surgical system 100 will be described in further detail below.

Control system 200 is also configured to receive information from user input mechanism 206. For example, control system 200 may receive information indicating a type of input received by way of user input mechanism 206. For example, if user input mechanism 206 is a button, the type of input from user input mechanism 206 may include a press of the button, a release of the button, a press and hold of the button, etc. Alternatively or additionally, the type of input received by way of user input mechanism 206 may include any suitable movement, actuation, and/or de-actuation of user input mechanism 206. The information regarding the type of input from user input mechanism 206 may indicate one input or more than one input received via user input mechanism 206, such as a single press, a single release, a press and a release, a double-press, etc. Control system 200 may receive or generate information indicating one or more times associated with input(s) received by way of user input mechanism 206, such as a timestamp indicating a time when an input was received.

Control system 200 includes a function selection system 208. Control system 200 may provide information to function selection system 208 for use by function selection system 208 to select (e.g., determine and activate) a desired function of the computer-assisted surgical system based on input received via user input mechanism 206 and information associated with user input mechanism 206 and user control mechanism 202 (e.g., contextual information).

Figure 3:
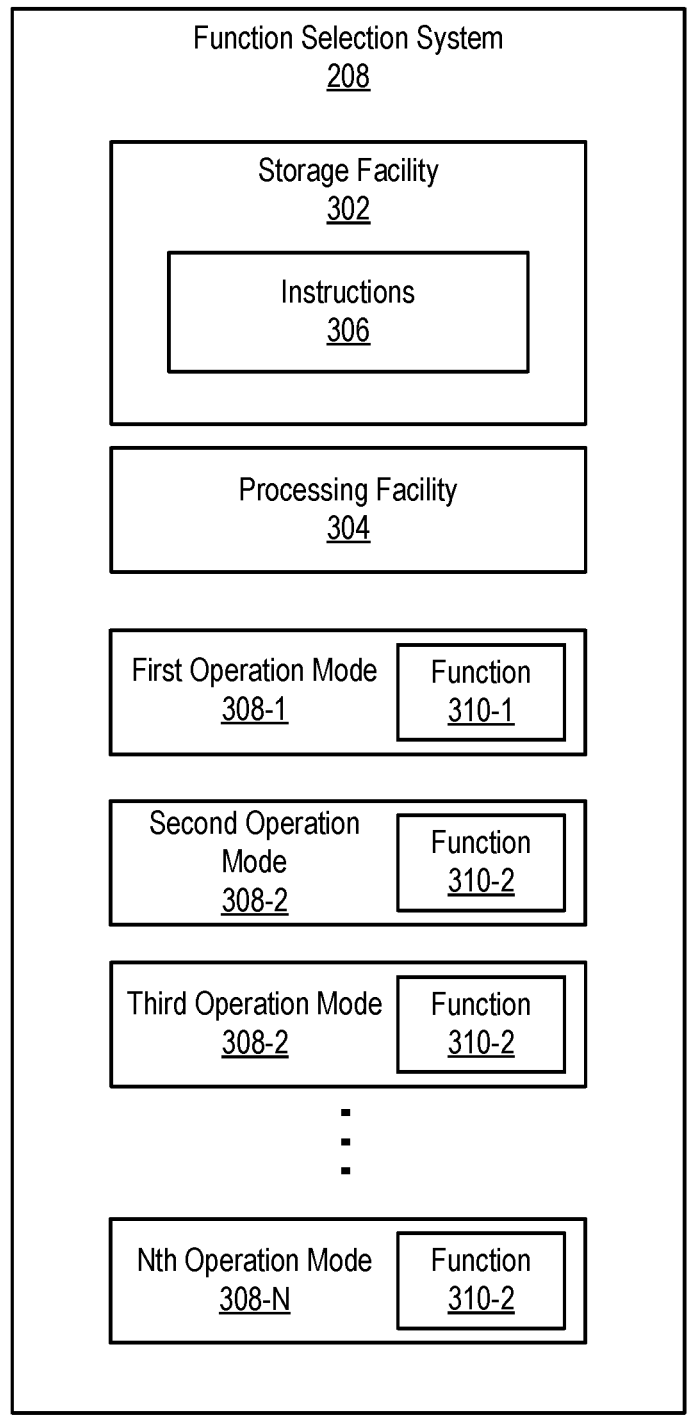
FIG. 3 illustrates an exemplary function selection system according to principles described herein.

FIG. 3 illustrates an exemplary function selection system 208 that may be configured to select a function of a computer-assisted surgical system to be performed. Function selection system 208 may be a part of control system 200 as in FIG. 2. Alternatively, function selection system 208 may be a separate system communicatively coupled to control system 200.

As shown in FIG. 3, function selection system 208 may include a storage facility 302, a processing facility 304, and operation modes 308 (operation modes 308-1 through 308-N). Storage facility 302 and processing facility 304 may be selectively and communicatively coupled to one another. Storage facility 302 and processing facility 304 may each include or be implemented by hardware and/or software components (e.g., processors, memories, communication interfaces, instructions stored in memory for execution by the processors, etc.). For example, storage facility 302 and processing facility 304 may be implemented by any component(s) of a computer-assisted surgical system.

Storage facility 302 may maintain (e.g., store) executable data used by processing facility 304 to perform any of the operations described herein. For example, storage facility 302 may store instructions 306 that may be executed by processing facility 304 to perform any of the operations described herein. Instructions 306 may be implemented by any suitable application, software, code, and/or other executable data instance. Storage facility 302 may also maintain any data received, generated, managed, used, and/or transmitted by processing facility 304.

Processing facility 304 may be configured to perform (e.g., execute instructions 306 stored in storage facility 302 to perform) various operations associated with selecting functions of a computer-assisted surgical system such as surgical system 100 to be performed. For example, processing facility 304 may process input and information received by function selection system 208 and select a function to be performed based on the input and information. Once processing facility 304 selects a function, function selection system 208 may notify control system 200 of the selected function. Control system 200 may respond by performing the selected function.

A function of a computer-assisted surgical system may include any function that may be performed by the computer-assisted surgical system. In certain examples, a function may include an activation or a deactivation of a mode of operation of the computer-assisted surgical system. In other examples, a function may include any other function associated with a mode of operation, such as a function that may be performed by the computer-assisted surgical system when operating in a particular mode of operation.

In certain examples, function selection system 208 may be configured to select an operation mode from among various available operation modes 308 for a computer-assisted surgical system such as surgical system 100. For example, function selection system 208 may be configured to select from a first operation mode 308-1, a second operation mode 308-2, a third operation mode 308-3, and an nth operation mode 308-N. In certain examples, operation modes 308 may include a normal mode of operation, a clutch mode of operation, a measurement mode of operation, various camera and/or visual modes of operation (e.g., different types of fluorescence visualization modes of operation), different types of movement modes of operation, etc.

As an example, first operation mode 308-1 may be a normal operation mode in which control system 200 is configured to translate input received via user control mechanism 202 to operations of manipulator arm 112 in a manner that allows a surgeon to telemanipulate surgical instrument 204. When the normal operation mode is activated, control system 200 may couple or otherwise engage user control mechanism 202 with manipulator arm 112 such that manipulations of user control mechanism 202 are translated into operations of manipulator arm 112 and surgical instrument 204. Hence, when the normal operation mode is activated, as a surgeon moves his or her fingers, wrists, and hands via master controls, control system 200 may control one or more manipulator arms 112 to telemanipulate one or more surgical instruments in a corresponding manner.

Second operation mode 308-2 may be, for example, a clutch operation mode in which control system 200 may decouple user control mechanism 202 from manipulator arm 112 in a manner that allows the surgeon to move user control mechanism 202 without causing corresponding movement of manipulator arm 112 or surgical instrument 204. For example, the surgeon may reposition his or her hands and/or master controls without moving the surgical instruments and may do so when the clutch mode of operation is activated.

Third operation mode 308-3 may be, for example, a measurement operation mode in which control system 200 may couple user control mechanism 202 to manipulator arm 112 in a manner that allows the surgeon to control surgical instrument 204 as in the normal mode of operation. Control system 200 may also allow the surgeon to measure distances in a surgical area using surgical instrument 204 (and optionally one or more other surgical instruments) when the measurement mode of operation is activated. For example, control system 200 may receive input specifying an indication of a starting point and an indication of an ending point and determine and provide a distance between the ending point and the starting point. Alternatively or additionally, control system 200 may receive input specifying an indication of a starting point and determine and provide a distance from the starting point to a current position of surgical instrument 204 as surgical instrument 204 is moved. For example, the indication of the starting point may be a point at which the measurement mode is activated by control system 200. Once control system 200 has activated the measurement mode of operation, the surgeon may be provided a visual indicator of distance from the starting point as the surgeon moves surgical instrument 204 via user control mechanism 202. In some examples, the surgeon may provide input indicating an ending point. In some examples, function selection system 208 may be configured to automatically deactivate the measurement mode of operation in response to detecting the indication of the ending point. Surgical system 100 may be configured to provide the distance measurement between the starting point and ending point as output in any suitable way (e.g., visually of a display screen) and/or store data representative of the distance measurement to a data storage.

Function selection system 208 may be configured to determine and activate an operation mode of control system 200. To this end, function selection system 208 may detect input received by way of user input mechanism 206 and select an operation mode based on information associated with user input mechanism 206 and user control mechanism 202.

For example, function selection system 208 may detect an input received by way of user input mechanism 206. Based on detecting the input, function selection system 208 may determine information associated with user input mechanism 206. For example, information associated with user input mechanism 206 may include a type of input received via user input mechanism 206, such as an actuation or de-actuation of user input mechanism 206. Information associated with user input mechanism 206 may also include a timestamp, such as a time when the input was received.

Based on detecting the input, function selection system 208 may also determine information associated with user control mechanism 202. Information associated with user control mechanism 202 may provide additional context of the input and may be used by function selection system 208 to select an operation mode. For example, information associated with user control mechanism 202 may include a position of user control mechanism 202, a movement of user control mechanism 202, a velocity of user control mechanism 202, etc. Function selection system 208 may determine information associated with user control mechanism 202 at any suitable time, including upon detecting receipt of input via user input mechanism 206, in response to one or more other events, and/or periodically at any suitable sampling rate.

Function selection system 208 may compare information associated with user input mechanism 206 and user control mechanism 202 to a set of defined criteria to determine an operation mode to be selected. The set of defined criteria may include any suitable set of criteria, such as a threshold distance, a threshold velocity, a threshold time, etc. The set of defined criteria may be defined in any suitable way (e.g., in advance of operation of control system 200) and as may suit a particular implementation. Examples of defined criteria are described herein.

Based on comparing the information associated with user input mechanism 206 and user control mechanism 202 to a set of defined criteria, function selection system 208 may determine and activate one or more operation modes of control system 200. Illustrative examples of how function selection system 208 may be configured to select operation modes based on input received by way of user input mechanism 206 and on comparison of information associated with user input mechanism 206 and user control mechanism 202 to a set of defined criteria are described herein.

In certain implementations, user input mechanism 206 may be configured to facilitate activation and deactivation of a clutch mode of operation in which user control mechanism 202 is decoupled from controlling a surgical instrument. The decoupling may decouple a coupling of user control mechanism 202 to the surgical instrument that exists when control system 200 operates in a normal mode of operation in which user control mechanism 202 may be manipulated to cause the surgical instrument to move correspondingly. The decoupling may be performed in any suitable way, including by physically, logically, or communicatively decoupling user control mechanism 202 from the manipulator arm 112 to which the surgical instrument is attached. When the clutch mode of operation is activated, control system 200 may decouple user control mechanism 202 from controlling the surgical instrument. When the clutch mode of operation is deactivated, control system 200 may couple user control mechanism 202 for controlling the surgical instrument.

Function selection system 208 may be configured to activate and deactivate the clutch mode of operation based on input received by way of user input mechanism 206. In certain examples, function selection system 208 may be configured to automatically and/or instantaneously activate the clutch operation mode when a surgeon actuates (e.g., presses) user input mechanism 206. In certain alternative examples, function selection system 208 may be configured to activate the clutch operation mode when a surgeon actuates (e.g., presses) and holds user input mechanism 206 at least a defined amount of time. In other alternative examples, function selection system 208 may be configured to activate the clutch operation mode when a surgeon actuates (e.g., presses) and holds user input mechanism and moves user control mechanism 202 at least a defined threshold distance while user input mechanism 206 is actuated.

Function selection system 208 may be configured to deactivate the clutch mode of operation based on input received by way of user input mechanism 206. In certain examples, function selection system 208 may be configured to automatically and/or instantaneously deactivate the clutch operation mode when the surgeon de-actuates (e.g., releases) user input mechanism 206, such as when the surgeon releases user input mechanism 206 to end an actuation (e.g., a press and hold) of user input mechanism 206.

In addition to user input mechanism 206 being configured to facilitate activation and deactivation of the clutch mode of operation, user input mechanism 206 may be configured to facilitate performance of a function associated with another mode of operation. The function may be any function that may be performed by the computer-assisted surgical system. For example, the function may include an activation or deactivation of another mode of operation, such as a measurement mode of operation or a particular visualization mode of operation, for example. As another example, the function may be a function that is performed when the computer-assisted surgical system is operating in another particular mode of operation, such as a measurement sampling function that is performed when operating in the measurement mode of operation. In certain examples, function selection system 208 may be configured to perform a function associated with another mode of operation (e.g., activating the mode of operation or performing a function within an active mode of operation) when a surgeon quickly (e.g., in less time than a predefined time threshold) actuates and de-actuates user input mechanism 206 while keeping user control mechanism 202 stationary (e.g., by not moving user control mechanism 202 more than a predefined distance threshold).

In certain examples, a held actuation of user input mechanism 206 may indicate that a surgeon intends to operate in the clutch mode of operation, and a quick actuation and de-actuation of user input mechanism 206 may indicate that the surgeon intends to invoke a function associated with another mode of operation, such as a function of the measurement mode of operation. In such examples, function selection system 208 may be configured to perform the function associated with the other operation mode when user input mechanism 206 is actuated and de-actuated quickly (e.g., in less time than a predefined time threshold) and user control mechanism 202 is stationary (e.g., is not moved more than a predefined distance threshold) when user input mechanism 206 is actuated and de-actuated.

In order to determine whether to perform the function associated with another mode of operation in response to input received by way of user input mechanism 206, function selection system 208 may determine contextual information associated with the input received by way of user input mechanism 206 and compare the information to a set of defined criteria. Based on the comparing, function selection system 208 may determine whether to perform the function. By determining and using contextual information associated with the input to determine whether to perform the function, function selection system 208 may ascertain the intent of a surgeon in providing input via user input mechanism 206 and in a manner that may allow the surgeon to intuitively and accurately choose, via the same user input mechanism 206 to which multiple, layered functions are mapped, one or more functions to be performed by the computer-assisted surgical system.

Function selection system 208 may determine an intended function by comparing the input and the associated information with the set of defined criteria. For example, if a quick press and release of user input mechanism 206 is configured to invoke a function of the measurement operation mode and a press and hold of user input mechanism 206 is configured to activate the clutch operation mode, function selection system 208 may determine, based on information associated with input received via user input mechanism 206, whether a detected press and release of user input mechanism 206 is intended as a quick press and release to invoke the function of the measurement operation mode or a press, hold, and release intended to activate the clutch operation mode.

For example, in some implementations, function selection system 208 may detect input via user input mechanism 206 and determine a type of input detected. If the input is a press of user input mechanism 206, function selection system 208 may determine a timestamp of the press, as well as a position and a velocity of user control mechanism 202 at the time of the press. If the input is a release of user input mechanism 206, function selection system 208 may determine a timestamp of the release, as well as a position and a velocity of user control mechanism 202 at the time of the release.

When a press and a release of user input mechanism 206 are detected, function selection system 208 may compare the timestamp, position, and velocity at the time of the release with the timestamp, position, and velocity at the time of the press to determine whether the surgeon intended a quick press of user input mechanism 206. If the difference between the timestamps is greater than a defined threshold time, function selection system 208 may determine that the surgeon did not intend a quick press and may not invoke a function mapped to a quick press. Additionally or alternatively, if the difference between the positions is greater than a defined threshold distance, function selection system 208 may determine that the surgeon did not intend a quick press and may not invoke a function mapped to a quick press. Additionally or alternatively, if one of the velocities is greater than a defined threshold velocity and/or a velocity at a time between the press and the release is greater than the defined threshold velocity, function selection system 208 may determine that the surgeon did not intend a quick press and may not invoke a function mapped to a quick press.

Conversely, function selection system 208 may invoke the function mapped to the quick press if the information satisfies the set of defined criteria, determining that the satisfaction of the set of defined criteria indicates that the surgeon intended a quick press of user input mechanism 206. For example, if the difference between the timestamps is less than the defined threshold time, the difference between the positions is less than the defined threshold distance, and the velocities (and any detected intervening velocities) are each less than the defined threshold velocity, function selection system 208 may determine that the surgeon intended a quick press and release and may perform the function associated with another operation mode.

In some embodiments, comparing information associated with user input mechanism 206 and user control mechanism 202 may enable function selection system 208 to determine inadvertent interactions with user input mechanism 206. For example, if a time difference between a press of user input mechanism 206 and a release of user input mechanism 206 is less than a threshold time, but a velocity of user control mechanism 202 at the time of the press and/or the time of the release is greater than a threshold velocity, function selection system 208 may determine that the surgeon inadvertently pressed and released user input mechanism 206 quickly, rather than intended to invoke a function mapped to a quick press and release of user input mechanism.

While the foregoing example describes invoking a function based on a quick press and release of user input mechanism 206, function selection system 208 may be configured to selectively invoke a function mapped to user input mechanism 206 based on any other suitable input received by user input mechanism 206 that can be differentiated, using contextual information, from input received by way of user input mechanism 206 that is configured to invoke other functionality, such as activation and/or deactivation of a clutch mode of operation.

In some examples, function selection system 208 may be configured to allow a surgeon to provide different inputs, by way of user input mechanism 206, to choose various functions to be performed. For example, system 208 may be configured to detect various inputs received by way of user input mechanism 206 and to select, based on the received inputs, one or more operation modes, from among a set of operation modes, to be activated. For example, an actuation and hold of user input mechanism 206 may activate a clutch mode of operation, while different length presses of user input mechanism 206 may activate different operation modes. Additionally or alternatively, quick presses of user input mechanism 206 may cycle through activation of different operation modes. Additionally or alternatively, a different number of successive quick presses of user input mechanism 206 (e.g., a double click) may activate different operation modes. This may allow additional functionality (e.g., a third layer of functionality) to be layered on user input mechanism 206.

Functionality may be mapped to user input mechanism 206 based on any suitable context of a computer-assisted surgical system. In some examples, contextual information may include a current mode of operation of the computer-assisted surgical system. For example, if control system 200 is currently operating in a normal mode of operation and a quick press and release of user input mechanism 206 is detected, function selection system 208 may perform a function mapped to a quick press and release of user input mechanism 206 in relation to the normal mode of operation, such as an activation of a measurement mode of operation, a visualization mode of operation, or another mode of operation. As another example, if the current operating mode is the measurement mode of operation when a quick press and release of user input mechanism 206 is detected, function selection system 208 may perform a function mapped to a quick press and release of user input mechanism 206 in relation to the measurement mode of operation, such as a measurement sampling function, a deactivation of the measurement mode of operation, or an activation of the normal mode of operation.

As another example, control system 200 may be operating in a first visual operation mode in which user control mechanism 202 is coupled to and configured to telemanipulate an imaging device (e.g., an endoscope) that captures imagery of a surgical scene that is displayed (e.g., in a stereoscopic viewer of user control system 104 of surgical system 100). Based on the current operating mode being the first visual operation mode and/or an imaging device being coupled to control mechanism 202, function selection system 208 may activate a second visual operation mode if a surgeon quickly presses user input mechanism 206 when control system 200 is operating in the first visual mode of operation. For example, function selection system 208 may activate a second visual operation mode such as a fluorescence imagery viewing mode in which surgical system 100 displays images of a surgical scene that are augmented using fluorescence illumination (e.g., fluorescence imagery received via a fluoroscope).

FIG. 3 illustrates a set of functions 610 (e.g., functions 610-1 through 610-N) associated with operation modes 608 of a computer-assisted surgical system. Function 310-1 may be any function associated with first mode of operation 308-1, such as an activation of first mode of operation 308-1, a deactivation of first mode of operation 308-1, or any function that may be performed when first mode of operation 308-1 is active. Function 310-2 may similarly be any function of second mode of operation 308-2, and so forth. For a measurement operation mode, for example, a function associated with the measurement operation mode may include an activation of the measurement operation mode, a deactivation of the measurement mode of operation, a measurement sampling performed when the measurement mode of operation is active, or the like.

Function selection system 208 may be configured to select a function to perform in response to a quick press and release of user input mechanism 206 based at least in part on a current mode of operation of a control system 200. For example, if a quick press and release of user input mechanism 206 is detected when a measurement mode of operation is active, function selection system 208 may perform a measurement sampling function of the measurement mode of operation. As another example, if a quick press and release of user input mechanism 206 is detected when a visualization mode of operation is active (e.g., when telemanipulation of an imaging device is active), function selection system 208 may activate perform a visualization function such as activating a particular visualization mode of operation like a fluorescence enhanced visualization mode of operation. These examples are illustrative only. Selection of a function to perform in response to a quick press and release of user input mechanism 206 may be based on any suitable context of a computer-assisted surgical system.

As mentioned, in certain implementations, an actuation of user input mechanism 206 may be configured to automatically activate a clutch mode of operation of a computer-assisted surgical system. In some examples, this may be performed globally regardless of how user input mechanisms 206 is actuated or of context associated with the actuation. Similarly, a de-actuation of user input mechanism 206 may be configured to automatically deactivate the clutch mode of operation of the computer-assisted surgical system. In such implementations, certain functionality of the computer-assisted surgical system may be layered on top of the activation and deactivation of the clutch mode of operation by being mapped to a quick press and release of user input mechanism 206 that satisfies a set of predefined criteria, such as any of the exemplary criteria described herein. Thus, when a quick press and release of user input mechanism 206 that satisfies a set of predefined criteria is detected, in addition to activating and deactivating the clutch mode of operation, function selection system 208 may perform one or more functions that are mapped to the quick press and release of user input mechanism 206.

The automatic activation and deactivation of the clutch mode of operation may provide one or more benefits to a function that is performed when a quick press and release of user input mechanism 206 is detected, and the function may assume that the clutch mode of operation is active when the function is invoked. For example, the automatic activation and deactivation of the clutch mode of operation may ensure that the surgical instrument 204 is not inadvertently moved when the function is performed, which may benefit the function. To illustrate, the function may include a measurement sampling during which it is desirable for the surgical instrument to not be inadvertently moved.

Because activation and deactivation of the clutch mode of operation is mapped to user input mechanism 206 associated with control mechanism 202 that may be manipulated by a single hand of an operation, activation and deactivation of the clutch mode of operation may be applied specifically to (e.g., only to) the surgical instrument 204 connected to control mechanism 202 associated with user input mechanism 206. In addition, one or more additional functions that are mapped to user input mechanism 206 associated with control mechanism 202 may be specific to the surgical instrument 204 connected to control mechanism 202 associated with user input mechanism 206. Moreover, any context that is considered for selecting a function to invoke when a quick press and release of user input mechanism 206 is detected may be specific to that user input mechanism 206, the control mechanism 202 associated with the user input mechanism 206, and/or the surgical instrument 204 connected to the control mechanism 202 (e.g., which surgical instrument or type of surgical instrument is connected).

While the foregoing examples describe illustrative implementations for selectively activating and deactivating a clutch mode of operation and selectively performing a function associated with another mode of operation (e.g., a measurement mode of operation, a fluorescence visualization mode of operation, etc.) based on user input received by way of user input mechanism 206, function selection system 208 may be configured differently in other examples. For example, the specific inputs for activating a clutch mode of operation and selectively performing a function associated with another mode of operation may be reversed. For instance, the clutch mode of operation may be activated on a quick press and release of user input mechanism 206, while a function associated with a different mode of operation may be activated by pressing and holding user input mechanism 206.

While in certain implementations an actuation of user input mechanism 206 may be configured to automatically activate a clutch mode of operation of a computer-assisted surgical system, in alternative implementations, function selection system 208 may be configured to selectively activate the clutch mode of operation based on contextual information associated with the actuation of user input mechanism 206. For example, if a quick press and release of user input mechanism 206 is detected, function selection system 208 may perform a function mapped to the quick press and release of user input mechanism 206 and may abstain from activating the clutch mode of operation. In certain examples, the function may include activating a mode of operation other than the clutch mode of operation.

Figure 4:
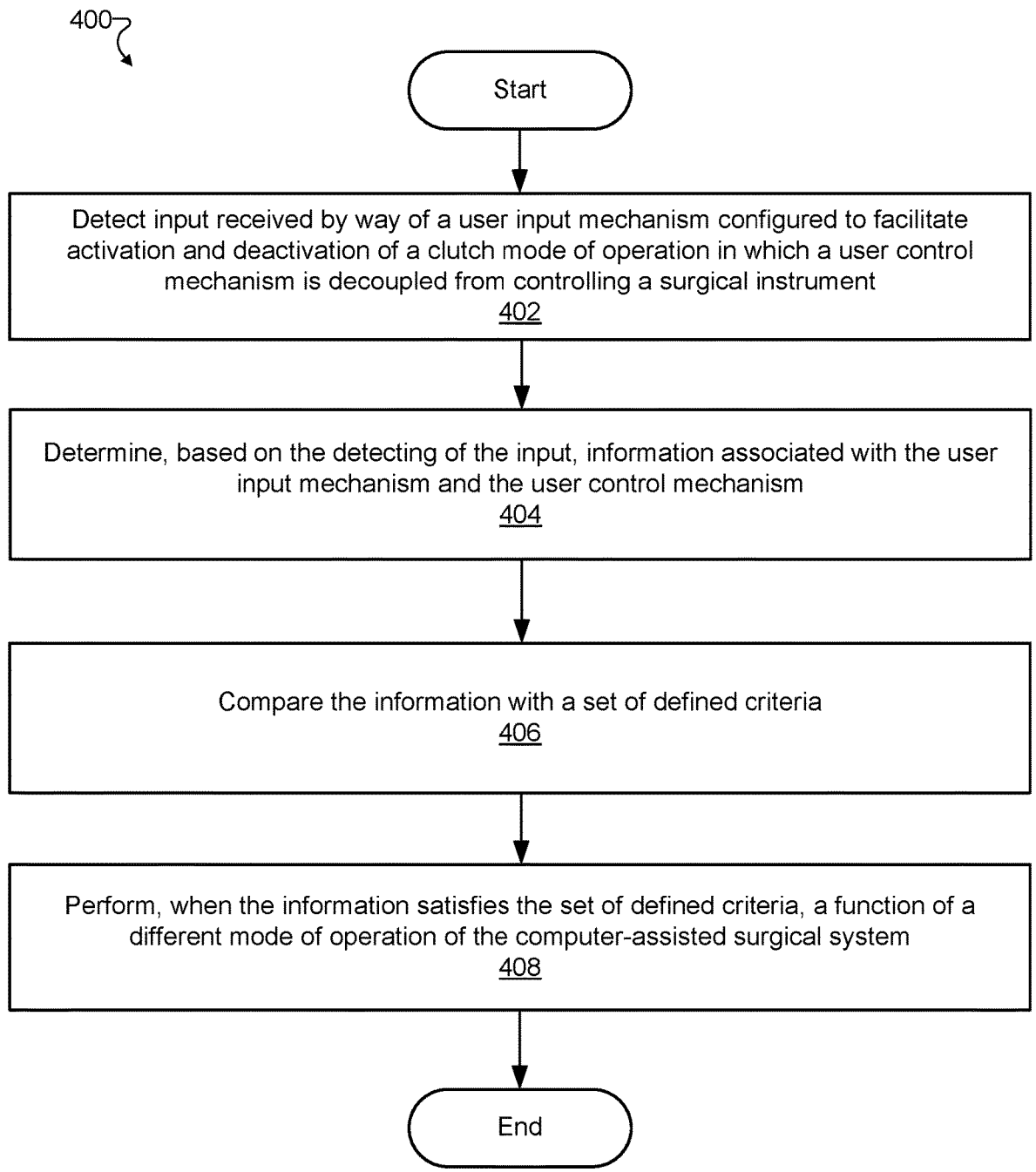
FIG. 4 illustrates an exemplary method for selectively performing a function of a computer-assisted surgical system according to principles described herein.

FIG. 4 illustrates an exemplary method 400 for selectively performing a function of a computer-assisted surgical system. While FIG. 4 illustrates exemplary operations according to one embodiment, other embodiments may omit, add to, reorder, and/or modify any of the operations shown in FIG. 4. One or more of the operations shown in FIG. 4 may be performed by function selection system 208, any components included therein, and/or any implementation thereof.

In operation 402, a function selection system detects input received by way of a user input mechanism (e.g., an actuation and a de-actuation of the user input mechanism) configured to facilitate activation and deactivation of a clutch mode of operation in which a user control mechanism is decoupled from controlling a surgical instrument. Operation 402 may be performed in any of the ways described herein.

In operation 404, the function selection system determines, based on the detecting of the input, information associated with the user input mechanism and the user control mechanism. Information associated with the user input mechanism and the user control mechanism may include any contextual information, examples of which have been described herein. Operation 404 may be performed in any of the ways described herein.

In operation 406, the function selection system compares the information with a set of defined criteria. Operation 406 may be performed in any of the ways described herein.

In operation 408, the function selection system performs, when the information satisfies the set of defined criteria, a function associated with a different mode of operation of the computer-assisted surgical system. Operation 408 may be performed in any of the ways described herein.

Figure 5:
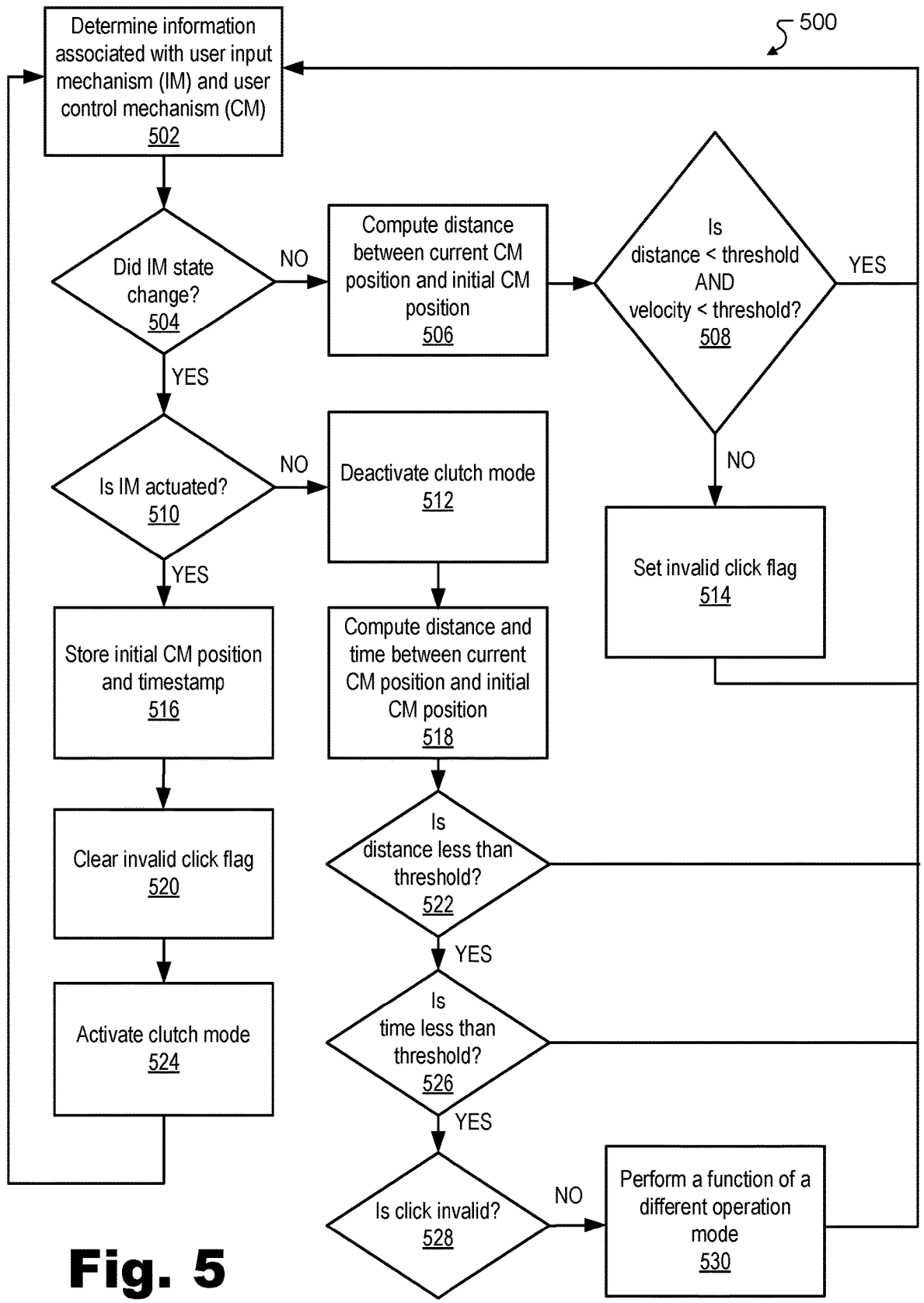
FIG. 5 illustrates an exemplary method for selectively performing a function of a computer-assisted surgical system according to principles described herein.

FIG. 5 illustrates an exemplary method 500 for selectively performing layered functions of a computer-assisted surgical system. While FIG. 5 illustrates exemplary operations according to one embodiment, other embodiments may omit, add to, reorder, and/or modify any of the operations shown in FIG. 5. One or more of the operations shown in FIG. 5 may be performed by function selection system 208, any components included therein, and/or any implementation thereof.

In exemplary method 500, the function selection system is configured to activate a clutch mode of operation ("clutch mode") upon detecting input indicating an actuation of a user input mechanism and to deactivate clutch mode upon detecting input indicating a de-actuation of the user input mechanism. Thus, any actuation of the user input mechanism activates clutch mode, and any de-actuation of the user input mechanism deactivates clutch mode. The function selection system determines upon de-actuation of the user input mechanism whether information associated with the inputs satisfies a set of defined criteria. If the set of defined criteria is determined to be satisfied, the function selection system activates a different operation mode (e.g., a measurement mode of operation, an augmented display mode of operation, etc.).

In operation 502, an function selection system determines information associated with a user input mechanism and a user control mechanism. In some examples, the function selection system may periodically (e.g., continually) sample to determine information such as whether input has been received via the user input mechanism, a position of the user control mechanism, and a velocity of the user control mechanism.

In operation 504, the function selection system determines whether a state of the user input mechanism has changed. For example, if the user input mechanism is a button, function selection system may determine whether the button has changed from pressed to released or vice versa. If the state of the user input mechanism has not changed, the function selection system may perform operation 506.

In operation 506, the function selection system computes a distance between a current position of the user control mechanism and an initial position of the user control mechanism that has been previously stored by the function selection system.

In operation 508, the function selection system compares the computed distance and determined velocity to a set of defined criteria. For example, the computed distance may be compared to a threshold distance and a determined velocity (e.g., a velocity determined in operation 502) may be compared to a threshold velocity. If the criteria are satisfied, the function selection system may return to operation 502 to continue sampling for information associated with the user input mechanism and the user control mechanism. If the criteria are not satisfied, for example a threshold is exceeded, an invalid click flag may be set in operation 514. An invalid click flag may be used to indicate that an actuation and de-actuation of the user input mechanism is not indicative of an intention to activate the different operation mode. For example, if a surgeon moves the user control mechanism beyond a threshold distance or faster than a threshold velocity, either while the user input mechanism is actuated or de-actuated, the function selection system may determine that the surgeon is not intending a quick press of the user input mechanism and thus set the invalid click flag. The invalid click flag may be included as contextual information associated with the user input mechanism.

Returning to operation 504, if the state of the user input mechanism is determined to have changed, the function selection system may perform operation 510. In operation 510, the function selection system detects a type of input of the user input mechanism. If the user input mechanism has been actuated (i.e., an actuated type input), the function selection system performs operation 516.

In operation 516, the function selection system stores a position of the user control mechanism and a timestamp of the received input. The function selection system may determine the position and the timestamp as the initial position and initial timestamp in any suitable way, including by using the position and timestamp last sampled in operation 502 or by sampling the position and time in response to detecting that the state of the user input mechanism changed in operation 504 or determining that the user input mechanism is actuated in operation 506. The stored position and timestamp may be used to compute distances, times, and velocities of the user control mechanism.

In operation 520, the function selection system clears the invalid click flag. As the received input is a new actuation of the user input mechanism, the function selection system may presume the click is valid until determined otherwise and may thus clear the invalid click flag to purge any determination of an invalid click from a previous actuation of the user input mechanism.

In operation 524, the function selection system activates clutch mode. As described above, in this example, the function selection system may activate clutch mode in response to any actuation of the user input mechanism. In this way, a surgeon may operate the surgical system in clutch mode upon actuation of the user input mechanism. After activating clutch mode in operation 524, the function selection system returns to operation 502 to continue sampling of the user input mechanism and the user control mechanism.

Returning to operation 510, if the state change of the user input mechanism is a de-actuation, the function selection system may deactivate clutch mode in operation 512. As described above, in this example, the function selection system may deactivate clutch mode in response to any de-actuation of the user input mechanism. In this way, a surgeon may cease to operate the surgical system in clutch mode upon de-actuation of the user input mechanism.

Upon deactivation of clutch mode, the function selection system may perform operation 518 in which the function selection system may compute a time between a timestamp of the de-actuation of clutch mode and the initial timestamp (e.g., an initial timestamp stored in operation 516 when the user input mechanism was actuated). The function selection system may also compute a distance between a current position of the user control mechanism and the stored initial position of the user control mechanism (e.g., an initial position stored in operation 516 when the user input mechanism was actuated).

In operation 522, the function selection system compares the computed distance with a threshold distance. The threshold distance in operation 522 may be the same or different from the threshold distance in operation 508. If the computed distance is more than (or greater than or equal to) the threshold distance, the function selection system may determine that the surgeon intended the clutch mode operation or that the actuation of the user input mechanism was inadvertent. The function selection system then returns to operation 502 to continue sampling. If the computed distance satisfies the defined criteria (e.g., is less than the threshold distance, is less than or equal to the threshold distance, etc.), the function selection system performs operation 526.

In operation 526, the function selection system compares the computed time with a threshold time. If the computed time is more than (or greater than or equal to) the threshold time, the function selection system may determine that the surgeon intended the clutch mode operation. The function selection system then returns to operation 502 to continue sampling. If the computed time satisfies the defined criteria (e.g., is less than the threshold time, is less than or equal to the threshold time, etc.), the function selection system performs operation 528.

In operation 528, the function selection system checks whether the invalid click flag is set. If the invalid click flag had been set previously and not cleared, it may indicate that the actuation of the user input mechanism was inadvertent. For example, the surgeon may actuate the user input mechanism, move the user control mechanism in a manner that returns the user control mechanism to a position within the threshold distance of the initial position in a time that is within the threshold time of the initial time. In such a case, the distance traveled by and/or the velocity of the user control mechanism between the actuation and the de-actuation would exceed the threshold distance or the threshold velocity (operation 508) such that the invalid click flag would have been set (operation 514). If the invalid click flag is set, the function selection system may determine that the actuation was inadvertent or that the surgeon did not intend to activate the different mode of operation and may return to operation 502. If the invalid click flag is not set, the function selection system may determine that the surgeon intended to perform a layered function associated with the different mode of operation, and the function selection system performs the layered function associated with the different mode of operation in operation 530. Operation 530 may be performed in any of the ways described herein.

In certain examples, a function selection system may be configured to perform one or more of the operations described herein at a servo rate (of a faster rate) of the user control mechanism to provide a certain level of temporal resolution and/or trajectory monitoring of small deviations of the user control mechanism. In other examples, an operation mode selection system may be configured to perform one or more of the operations described herein at any suitable rate.

In certain examples, a function selection system may be configured to use threshold values such as a distance threshold of two millimeters, a velocity threshold of two millimeters per second, and a time threshold of 0.5 seconds. Such threshold values may be included, in any suitable way, in a defined set of criteria and used by the operation mode selection system for comparisons of inputs and information associated with the user input mechanism and the user control mechanism to determine when to activate or not activate a mode of operation. Any other suitable threshold values may be used in other examples.

In certain embodiments, one or more of the systems, components, and/or processes described herein may be implemented and/or performed by one or more appropriately configured computing devices. To this end, one or more of the systems and/or components described above may include or be implemented by any computer hardware and/or computer-implemented instructions (e.g., software) embodied on at least one non-transitory computer-readable medium configured to perform one or more of the processes described herein. In particular, system components may be implemented on one physical computing device or may be implemented on more than one physical computing device. Accordingly, system components may include any number of computing devices, and may employ any of a number of computer operating systems.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory ("DRAM"), which typically constitutes a main memory. Common forms of computer-readable media include, for example, a disk, hard disk, magnetic tape, any other magnetic medium, a compact disc read-only memory ("CD-ROM"), a digital video disc ("DVD"), any other optical medium, random access memory ("RAM"), programmable read-only memory ("PROM"), electrically erasable programmable read-only memory ("EPROM"), FLASH-EEPROM, any other memory chip or cartridge, or any other tangible medium from which a computer can read.

Figure 6:
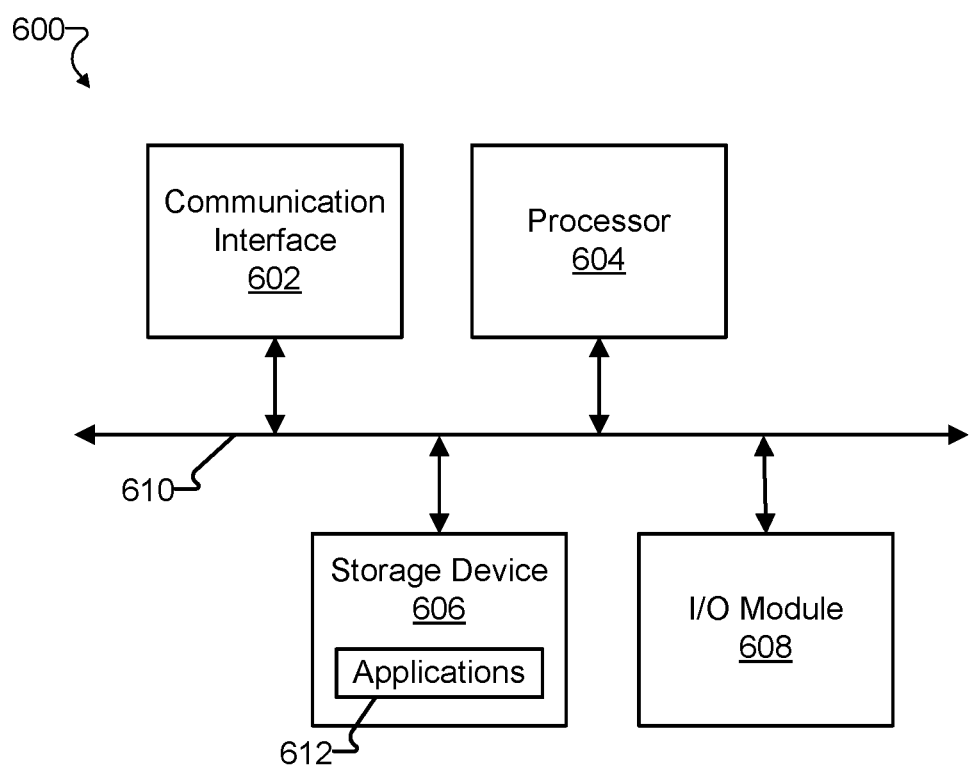
FIG. 6 illustrates an exemplary computing system according to principles described herein.

FIG. 6 illustrates an exemplary computing device 600 that may be specifically configured to perform one or more of the processes described herein. As shown in FIG. 6, computing device 600 may include a communication interface 602, a processor 604, a storage device 606, and an input/output ("I/O") module 608 communicatively connected via a communication infrastructure 610. While an exemplary computing device 600 is shown in FIG. 6, the components illustrated in FIG. 6 are not intended to be limiting. Additional or alternative components may be used in other embodiments. Components of computing device 600 shown in FIG. 6 will now be described in additional detail.

Communication interface 602 may be configured to communicate with one or more computing devices. Examples of communication interface 602 include, without limitation, a wired network interface (such as a network interface card), a wireless network interface (such as a wireless network interface card), a modem, an audio/video connection, and any other suitable interface.

Processor 604 generally represents any type or form of processing unit capable of processing data or interpreting, executing, and/or directing execution of one or more of the instructions, processes, and/or operations described herein. Processor 604 may direct execution of operations in accordance with one or more applications 612 or other computer-executable instructions such as may be stored in storage device 606 or another computer-readable medium.

Storage device 606 may include one or more data storage media, devices, or configurations and may employ any type, form, and combination of data storage media and/or device. For example, storage device 606 may include, but is not limited to, a hard drive, network drive, flash drive, magnetic disc, optical disc, RAM, dynamic RAM, other non-volatile and/or volatile data storage units, or a combination or sub-combination thereof. Electronic data, including data described herein, may be temporarily and/or permanently stored in storage device 606. For example, data representative of one or more executable applications 612 configured to direct processor 604 to perform any of the operations described herein may be stored within storage device 606. In some examples, data may be arranged in one or more databases residing within storage device 606.

I/O module 608 may include one or more I/O modules configured to receive user input and provide user output. One or more I/O modules may be used to receive input for a single virtual reality experience. I/O module 608 may include any hardware, firmware, software, or combination thereof supportive of input and output capabilities. For example, I/O module 608 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 608 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 608 is configured to provide graphical data to a display for presentation to a user. The graphical data may be representative of one or more graphical user interfaces and/or any other graphical content as may serve a particular implementation.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a memory storing instructions;
a processor communicatively coupled to the memory and configured to execute the instructions to:
detect user input received by way of a user input mechanism associated with a user control mechanism for controlling a surgical instrument coupled to a manipulator arm of a computer-assisted surgical system, the processor configured to activate, based on user interaction with the user input mechanism, a mode of operation in which the user control mechanism is repositionable without causing the surgical instrument to move;
determine, based on the detecting of the user input, information associated with the user input mechanism and the user control mechanism;
compare the information to a set of defined criteria; and
perform, when the information satisfies the set of defined criteria, a function associated with a different mode of operation of the computer-assisted surgical system.

2. The system of claim 1, wherein the information associated with the user control mechanism comprises:
information indicating that a type of the user input received is an actuation of the user input mechanism; and
information indicating a movement of the user control mechanism while the user input mechanism is actuated.

3. The system of claim 2, wherein:
the set of defined criteria comprises a defined threshold distance; and
the comparing of the information to the set of defined criteria comprises determining whether the movement of the user control mechanism while the user input mechanism is actuated satisfies the defined threshold distance.

4. The system of claim 1, wherein:
the set of defined criteria comprises a defined threshold time;
the user input received by way of the user input mechanism comprises a first input and a second input;
the information associated with the user control mechanism includes a first timestamp indicating when the first input is received and a second timestamp indicating when the second input is received; and
the comparing of the information to the set of defined criteria comprises determining whether a time difference between the first timestamp and the second timestamp satisfies the defined threshold time.

5. The system of claim 1, wherein:
the set of defined criteria comprises a defined threshold distance;
the user input received by way of the user input mechanism comprises a first input and a second input;
the information associated with the user control mechanism includes a first position indicating a position of the user control mechanism when the first input is received and a second position indicating a position of the user control mechanism when the second input is received; and the comparing of the information to the set of defined criteria comprises determining whether a distance difference between the first position and the second position satisfies the defined threshold distance.

6. The system of claim 1, wherein:
the set of defined criteria comprises a defined threshold velocity;
the information associated with and the user control mechanism includes information indicating a velocity of the user control mechanism; and
the comparing of the information to the set of defined criteria comprises determining whether the velocity satisfies the defined threshold velocity.

7. The system of claim 1, wherein the processor is configured to automatically activate the mode of operation in which the user control mechanism is repositionable without causing the surgical instrument to move upon an actuation of the user input mechanism and deactivate the mode of operation upon a de-actuation of the user input mechanism.

8. The system of claim 1, wherein the different mode of operation includes a measurement mode of operation in which the surgical instrument is configured to be used to measure a distance between two points.

9. The system of claim 1, wherein the different mode of operation includes a viewing mode of operation in which a display of imagery of a surgical scene is augmented using fluorescence illumination.

10. A non-transitory computer-readable medium storing instructions that, when executed, direct at least one processor of a computing device to:
detect a first input received by way of a user input mechanism associated with a user control mechanism for controlling a surgical instrument coupled to a manipulator arm of a computer-assisted surgical system, the user input mechanism configured to facilitate activation and deactivation of a clutch mode of operation in which the user control mechanism is decoupled from controlling the surgical instrument;
determine, based on the detecting of the first input, a first set of information associated with the user input mechanism and the user control mechanism;
detect a second input received by way of the user input mechanism;
determine, based on the detecting of the second input, a second set of information associated with the user input mechanism and the user control mechanism;
compare the first set of information and the second set of information to a set of defined criteria; and
perform, when the set of defined criteria is satisfied, a function associated with a different mode of operation of the computer-assisted surgical system.

11. The computer-readable medium of claim 10, wherein:
the first set of information associated with the user input mechanism and the user control mechanism includes information indicating that the first input received is an actuation of the user input mechanism; and
the second set of information associated with the user input mechanism and the user control mechanism includes information indicating that the second input received is a de-actuation of the user input mechanism.

12. The computer-readable medium of claim 10, wherein:
the set of defined criteria comprises a defined threshold time;
the first set of information associated with the user input mechanism and the user control mechanism includes a first timestamp indicating when the first input is received by way of the user input mechanism;
the second set of information associated with the user input mechanism and the user control mechanism includes a second timestamp indicating when the second input is received by way of the user input mechanism; and
the comparing the first set of information and the second set of information to the set of defined criteria comprises determining whether a time difference between the first timestamp and the second timestamp satisfies the defined threshold time.

13. The computer-readable medium of claim 10, wherein:
the set of defined criteria comprises a defined threshold distance;
the first set of information associated with the user input mechanism and the user control mechanism includes information indicating a first position of the user control mechanism when the first input is received by way of the user input mechanism;
the second set of information associated with the user input mechanism and the user control mechanism includes information indicating a second position of the user control mechanism when the second input is received by way of the user input mechanism; and
the comparing the first set of information and the second set of information to the set of defined criteria comprises determining whether a distance difference between the first position and the second position satisfies the defined threshold distance.

14. The computer-readable medium of claim 10, wherein:
the set of defined criteria comprises a defined threshold velocity;
the first set of information associated with the user input mechanism and the user control mechanism includes a first velocity of the user control mechanism when the first input is received by way of the user input mechanism;
the second set of information associated with the user input mechanism and the user control mechanism includes a second velocity of the user control mechanism when the second input is received by way of the user input mechanism; and
the comparing the first set of information and the second set of information to the set of defined criteria comprises determining whether the first velocity or the second velocity satisfies the defined threshold velocity.

15. A method comprising:
detecting user input received by way of a user input mechanism associated with a user control mechanism for controlling a surgical instrument coupled to a manipulator arm of a computer-assisted surgical system, a processor configured to activate, based on user interaction with the user input mechanism, a mode of operation in which the user control mechanism is repositionable without causing the surgical instrument to move;
determining, based on the detecting of the user input, information associated with the user input mechanism and the user control mechanism;
comparing the information to a set of defined criteria; and
performing, when the information satisfies the set of defined criteria, a function associated with a different mode of operation of the computer-assisted surgical system.

16. The method of claim 15, wherein the information associated with the user control mechanism comprises:

information indicating that a type of the user input received is an actuation of the user input mechanism; and information indicating a movement of the user control mechanism while the user input is actuated.

17. The method of claim 15, wherein the processor is configured to automatically activate the mode of operation in which the user control mechanism is repositionable without causing the surgical instrument to move upon detecting an actuation of the user input mechanism and deactivating the clutch mode of operation upon detecting a de-actuation of the user input mechanism.

18. The method of claim 17, wherein:

the information associated with the user input mechanism and the user control mechanism includes:

at least one of a first timestamp indicating when the actuation is received and a first position indicating a position of the user control mechanism when the actuation is received; and at least one of a second timestamp indicating when the de-actuation is received and a second position indicating a position of the user control mechanism when the de-actuation is received; and the comparing of the information to the set of defined criteria comprises at least one of determining whether a time difference between the first timestamp and the second timestamp satisfies a defined threshold time and determining whether a distance difference between the first position and the second position satisfies a defined threshold distance.

19. The method of claim 17, wherein:

the different mode of operation includes a measurement mode in which the surgical instrument is configured to be used to measure a distance between two points; and the function comprises at least one of an activation of the measurement mode and a measurement sampling of the measurement mode.

20. The method of claim 17, wherein the different mode of operation includes a viewing mode in which a display of imagery of a surgical scene is augmented using fluorescence illumination.

* * * * *